(12) United States Patent
Tofighi et al.

(10) Patent No.: US 7,318,841 B2
(45) Date of Patent: Jan. 15, 2008

(54) SYNTHESIS OF CALCIUM PHOSPHATES BY MECHANO-CHEMICAL PROCESS

(75) Inventors: Aliassghar Tofighi, Waltham, MA (US); Christian Rey, Castanet (FR)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 10/222,670

(22) Filed: Aug. 16, 2002

(65) Prior Publication Data

US 2003/0120351 A1   Jun. 26, 2003

Related U.S. Application Data

(63) Continuation-in-part of application No. 10/027,656, filed on Dec. 21, 2001, now Pat. No. 6,840,951.

(51) Int. Cl.
*A61F 2/28* (2006.01)

(52) U.S. Cl. .................................................. 623/23.62

(58) Field of Classification Search ............ 623/23.51, 623/23.61, 23.62; 423/299, 308, 311; 424/602
See application file for complete search history.

(56) References Cited

U.S. PATENT DOCUMENTS

| | | | | |
|---|---|---|---|---|
| 4,518,430 A | * | 5/1985 | Brown et al. ................. 106/35 |
| RE33,221 E | * | 5/1990 | Brown et al. ................. 423/308 |
| 5,053,212 A | | 10/1991 | Constantz et al. |
| 5,383,615 A | | 1/1995 | Calka et al. ................. 241/172 |
| 5,508,342 A | | 4/1996 | Antonucci et al. .......... 524/788 |
| 5,605,713 A | * | 2/1997 | Boltong ....................... 427/2.1 |
| 5,650,176 A | | 7/1997 | Lee et al. .................... 424/602 |
| 5,676,976 A | | 10/1997 | Lee et al. .................... 424/602 |
| 5,679,294 A | | 10/1997 | Umezu et al. ................ 264/44 |
| 5,683,461 A | | 11/1997 | Lee et al. ..................... 623/16 |
| 5,697,981 A | * | 12/1997 | Ison et al. .................... 606/63 |
| 5,782,971 A | * | 7/1998 | Constantz et al. .......... 106/690 |
| 5,837,030 A | | 11/1998 | Schulz et al. ................ 75/352 |
| 5,872,074 A | | 2/1999 | Schulz et al. ............... 502/328 |
| 5,900,254 A | | 5/1999 | Constantz ................... 424/602 |
| 5,916,381 A | | 6/1999 | Sapru et al. ................. 148/403 |
| 6,005,162 A | | 12/1999 | Constantz .................... 623/16 |
| 6,017,504 A | | 1/2000 | Kaliaguine et al. ......... 423/263 |
| 6,027,742 A | | 2/2000 | Lee et al. .................... 424/602 |
| 6,117,456 A | | 9/2000 | Lee et al. .................... 424/602 |
| 6,132,463 A | | 10/2000 | Lee et al. ..................... 623/16 |
| 6,139,578 A | | 10/2000 | Lee et al. ................. 623/16.11 |
| 6,201,039 B1 | | 3/2001 | Brown et al. |
| 6,214,368 B1 | | 4/2001 | Lee et al. .................... 424/423 |
| 6,277,151 B1 | | 8/2001 | Lee et al. ................. 623/23.61 |
| 6,287,341 B1 | | 9/2001 | Lee et al. ................. 623/16.11 |
| 6,331,312 B1 | | 12/2001 | Lee et al. .................... 424/426 |
| 6,334,891 B1 | | 1/2002 | Constantz et al. ............ 106/35 |
| 6,478,825 B1 | * | 11/2002 | Winterbottom et al. .. 623/23.63 |
| 6,642,285 B1 | * | 11/2003 | Bohner ........................ 523/115 |
| 6,703,038 B1 | * | 3/2004 | Schaefer et al. ............ 424/426 |
| 6,720,023 B1 | * | 4/2004 | Kim et al. ................. 427/2.27 |
| 6,723,334 B1 | * | 4/2004 | McGee et al. .............. 424/423 |

* cited by examiner

*Primary Examiner*—Anuradha Ramana
(74) *Attorney, Agent, or Firm*—Clark & Elbing LLP

(57) ABSTRACT

A low crystallinity calcium phosphate powder is prepared by mechanically grinding a calcium phosphate solid under grinding forces local heating sufficient to mechanically alloy the calcium phosphate solid and reduce the crystalline domains of the calcium phosphate solid to less than about 100 nm. The method is useful for making any calcium phosphate material by solid-solid mixing and high energy grinding.

20 Claims, 13 Drawing Sheets

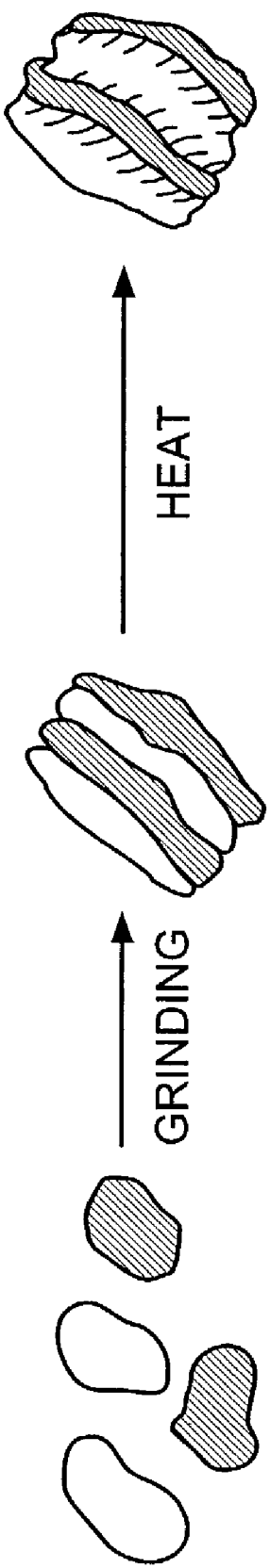

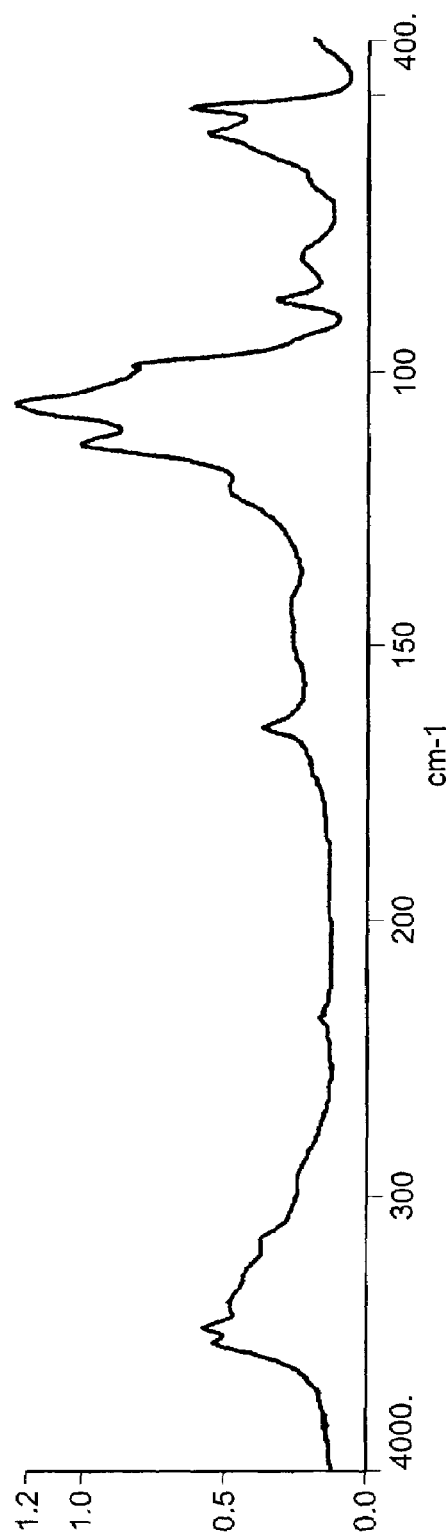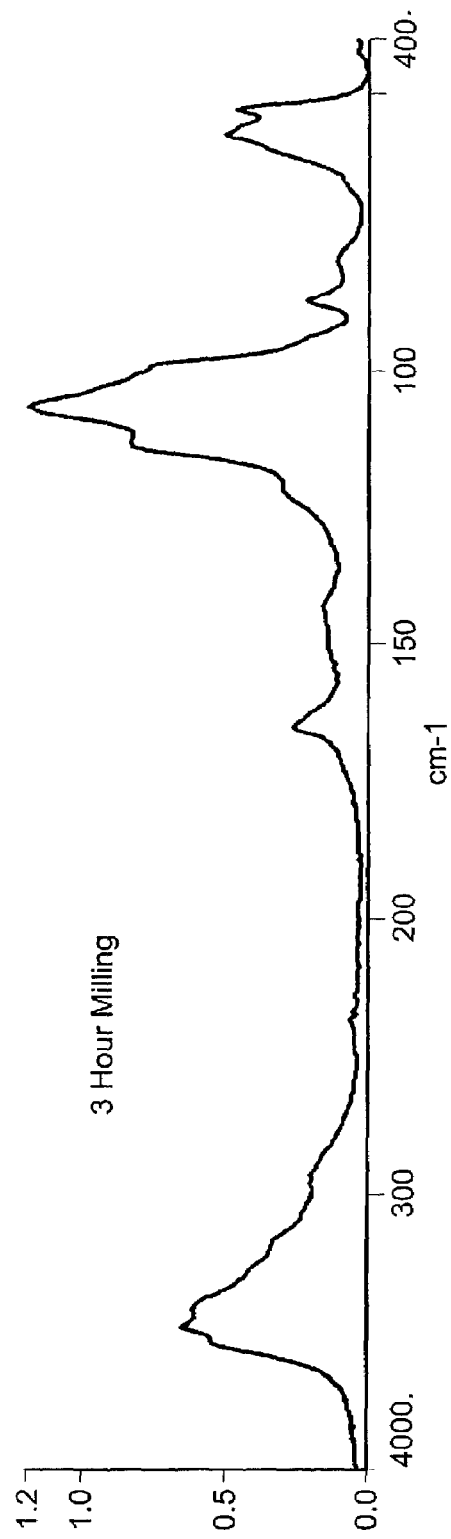

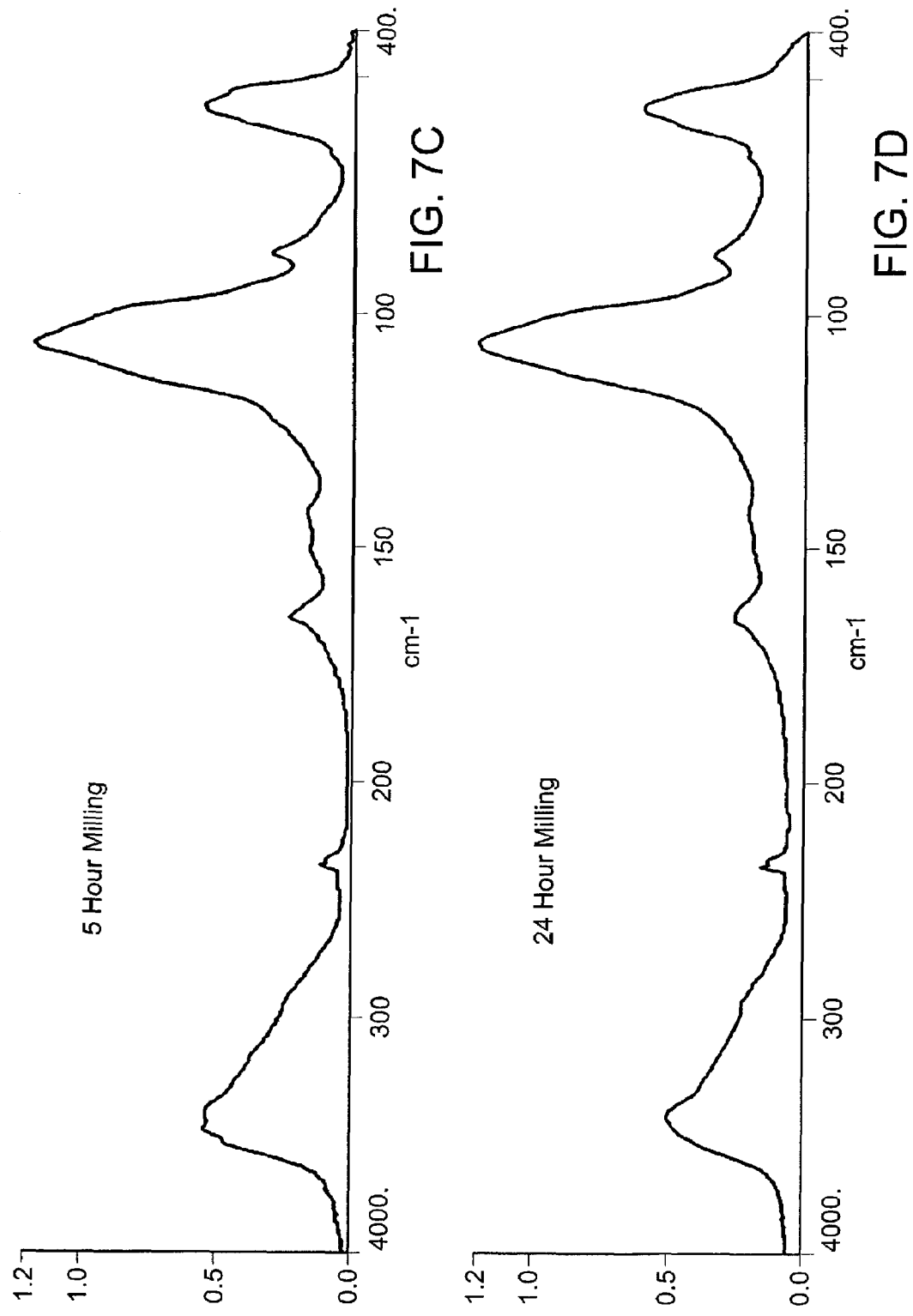

SYNTHESIS OF CALCIUM PHOSPHATES BY MECHANO-CHEMICAL PROCESS

RELATED APPLICATIONS

This application is a continuation-in-part application of application U.S. Ser. No. 10/027,656, filed Dec. 21, 2001 now U.S. Pat. No. 6,840,951, which is incorporated in its entirety by reference.

BACKGROUND OF THE INVENTION

1. Field of the Invention

The field of the present invention is bone repair and replacement. More specifically, the invention relates to nanocrystalline calcium phosphate powders useful as bone substitute materials and methods of their manufacture.

2. Description of the Related Art

Naturally-occurring bone mineral is made of nanometer-sized, poorly-crystalline apatitic calcium phosphate with a Ca/P ratio between 1.45 and 1.75. See, Besic et al. *J. Dental Res.* 48(1):131 (1969). These properties impart solubility to bone tissue that allows it to be repaired continually by osteoclasts and osteoblasts. Natural bone grafts are incorporated into a patient's bone through this continual remodeling process in vivo. However, natural bone grafts are associated with problems such as limited availability and painful, risky harvesting procedures for a patient's own autogenous bone, and risks of viral transmission and immune reaction for allograft bone from a cadaver.

Synthetic bone graft materials have been used to avoid the problems associated with natural bone grafts. Desirable properties for synthetic bone graft materials include biocompatibility with natural bone; structural integrity, so that the graft remains in place and intact until bone heals around it; resorbability, so that the graft material is replaced by bone and is accessible to osteoclasts, osteoblasts, and other bone-forming cells; and compatibility with low-temperature processing, which is desired for incorporating heat-sensitive bone growth proteins or other growth factors.

Bioceramics have been used as bone graft substitute materials. Most commonly used have been calcium phosphate ceramics, such as hydroxyapatite and tricalcium phosphate. Highly crystalline hydroxyapatite is dense, and therefore strong. Such crystalline hydroxyapatite is essentially non-resorbable in vivo, and thus is not replaced by natural bone. Hydroxyapatite solids of lower crystallinity have been reported that are resorbable and chemically similar to the mineral component of natural bone. However, these materials are not strong enough for load bearing applications or other applications requiring high-strength materials. Similarly, tricalcium phosphate materials generally are degraded rapidly in vivo, but lack sufficient strength for weight-bearing applications. Combinations of hydroxyapatite and tricalcium phosphate have been reported, which attempt to mitigate the shortcomings of the individual calcium phosphate components.

Recent developments in bone graft substitute materials include the use of amorphous calcium phosphates. Compositions for use in skeletal repair including an amorphous calcium phosphate and a crosslinkable organic polymer have been reported. Amorphous calcium phosphates have also been combined with more crystalline calcium phosphates to form self-setting ceramic cements. In these cases, preparation of amorphous calcium phosphate is accomplished by low temperature double decomposition between calcium and phosphate ion sources, typically under basic conditions.

New sources for low crystallinity or amorphous calcium phosphate powders for use as bone substitute materials are needed. In particular, nanocrystalline calcium phosphate materials useful in the preparation of high strength calcium phosphate articles are desired.

The preparation of metal alloys by intensive grinding (or milling) of a mixture of metal powders, also called mechanical alloying or mechanical grinding, is a well-known technique. Ball mills and attritors are used to produce fine powders. Ball milling also is used to promote solid state reactions, which result in synthesis of new alloys from elemental powders, or to alter the alloy structure.

When mechanical alloying is used to produce new materials, there is a combination of repeated welding, fracturing and rewelding of the mixture of powder particles mixtures, thereby providing powders of a fine microstructure and facilitating rapid interdiffusion between the particles. Mechanical alloying has been used to form finely divided metal alloys and to promote the formation of intermetallic compounds. High energy milling has even been reported for ceramic materials, for example, to induce chemical reactions between the component ceramic powders and thereby synthesize fine particle-size reacted product.

SUMMARY OF THE INVENTION

One aspect the present invention provides a method of forming an amorphous or nanocrystalline calcium phosphate powder by high energy grinding of a crystalline calcium phosphate solid under grinding forces and locally generated heat sufficient to mechanically alloy the calcium phosphate solid and to reduce the crystalline domains of the calcium phosphate solid to less than about 100 nm, hereinafter the "amorphicized powder." In one or more embodiments, the grinding process produces an amorphous calcium phosphate structure.

In another aspect of the present invention, a single-component self-setting calcium phosphate cement is provided. The amorphicized calcium phosphate powder is highly reactive and is capable of setting into a hardened calcium phosphate cement. A single-component calcium phosphate is a powder that includes a calcium phosphate from a single chemical source. This is distinguished from a powder having multiple calcium phosphate sources, even if they are combined physically into a single powder. In one or more embodiments, the single-component cement forms an apatitic calcium phosphate after hydration.

In another aspect of the present invention, a multi-component self-setting calcium phosphate cement is provided. The cement includes a calcium phosphate solid and a second solid selected from the group consisting of a calcium source, a phosphate source and a calcium phosphate source and a carrier fluid in an amount sufficient to form a malleable paste, characterized in that the paste hardens at body temperature in less than 30 minutes. The calcium phosphate solid and the second solid in combination have a calcium to phosphorus atomic ratio in the range of 1:1 to 2:1. The calcium phosphate solid and the second solid have an average crystalline domain size of less than about 100 nm.

In one or more embodiments of the present invention, the amorphicized powder is used to form a high compressive strength calcium phosphate cement. The amorphicized powder is combined with sufficient carrier liquid to form a malleable paste. Optionally, additional dry powder components needed to form a hardened calcium phosphate product or to impart other additional properties to the article are included. The paste hardens into a calcium phosphate cement at room or body temperature. The compressive strength of the resultant product is increased relative to that of a product prepared from calcium phosphate solids that are crystalline and that have not been subjected to the high energy grinding of one or more embodiments of the present invention.

In one or more embodiments; the compressive strength of the hardened phosphate produce is greater than 20 MPa, greater than 30 MPa, or in the range of 30-50 MPa after incubated in a moist environment at 37° C.

"Crystallinity" is the state of a solid material characterized by a periodic and repeating three-dimensional arrays of atoms, ions, or molecules. As used herein, a "crystallite" or "crystalline domain" is a region within a particle or solid material in which all the atoms, ions or molecular chains are substantially ordered and aligned. The crystalline domains of the particles of the invention are small, i.e., on the scale of 10 s or 100 s of nanometers.

The term "nanocrystalline" as used herein describes any kind of powder consisting of crystallites or crystalline domains of very small crystal size, e.g., a size smaller than about 100 nm.

The term "amorphous" as used herein describes any kind of powder having no or little discernible long-range atomic order. The degree of crystallinity or crystallinity index can be determined by X-ray diffraction (XRD). Amorphous materials are characterized by a broad, featureless XRD pattern. See, for example, FIG. 2B and FIG. 6B.

The term "about" as used herein refers to ±10% of the recited value.

As can be appreciated, the process according to the present invention is simple, efficient, and inexpensive and produces an amorphous or nanocrystalline calcium phosphate that may easily show a very high specific surface area and increased reactivity. The reduced particle size also increases the packing efficiency, density and hardness of the resultant hardened cement. Any calcium phosphate composition can be attained using calcium sources and phosphate sources in the appropriate Ca:P atomic ratio. These and other features of the methods and compositions of the present invention impart advantages to a self-setting calcium phosphate cement as is described in greater detail below.

BRIEF DESCRIPTION OF THE DRAWINGS

The invention is described with reference to the following figures, which are presented for the purpose of illustration only and which are not intended to be limiting of the invention.

FIG. 1 is a pictorial illustration of the mechanical alloying process in one or more embodiments of the present invention;

FIGS. 7A-D illustrate the Fourier Transform infrared (FTIR) spectrum of (7A) a physical mixture of amorphous calcium phosphate and dicalcium phosphate dihydrate (DCPD), the same amorphous calcium phosphate and DCPD mixture after (7B) 3 hours, (7C) 5 hours, and (7D) 24 hours of high energy grinding to obtain a powder of increasing amorphicity.

DETAILED DESCRIPTION OF THE INVENTION

Figure 2A:
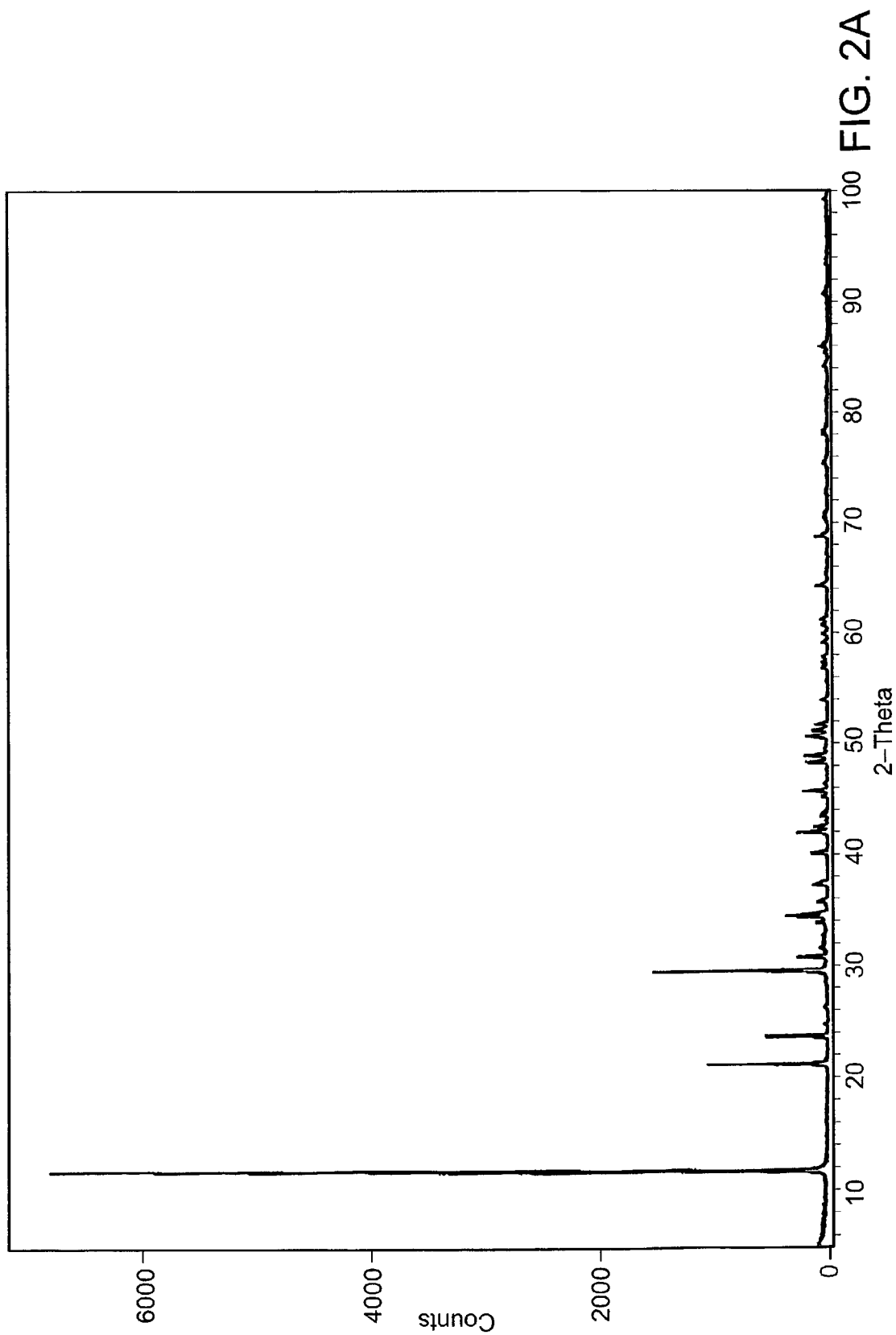
FIGS. 2A and 2B illustrate x-ray diffraction (XRD) pattern of dicalcium phosphate dihydrate (DCPD) (2A) before and (2B) after high energy milling at 400 RPM for 20 minutes in a high energy ball mill.

According to one or more embodiments of the present invention, an amorphous or nanocrystalline calcium phosphate powder is obtained by high energy grinding of a calcium phosphate solid under forces sufficient to mechanically fuse the calcium phosphate solid and to reduce the crystalline domains of the calcium phosphate solid to less than about 100 nm. This process is used in the compositions and methods of the present invention to provide single- and multi-component calcium phosphate powders that have reduced crystallinity, reduced particle size and modified solid state structures. Because the resultant powders have considerably reduced crystallinity, the process is referred to as "amorphization" and the powders are referred to herein as "amorphicized powders." These changes are used to control the rate of hardening, setting, extent of reaction and/or the hardness of the final product.

During mechanically alloying (or solid-solid fusion) the particles experience multiple impacts with other particles so that the particles are broken down into much smaller, high specific surface area particles and so that interdiffusion of the particles occurs. The transfer of energy into the powder leads to material transformations such as, by way of example only, atomic dislocations, structure defects of the lattice and magnification or the surface boundary layer. In one or more embodiments of the invention, interdiffusion is accompanied by a change in the structure and/or composition of the calcium phosphate solids. As is shown in FIG. 1, high energy mechanical grinding of powders (shown in black and white) allows the formation of a mechanically alloyed structure. Simultaneous collision and local heating causes an interdiffusion of the particles (shown in dotted lines) leading to structural (crystalline) and chemical changes within the particles.

In one or more embodiments of the present invention, a single calcium phosphate source is subjected to amorphization. It may be desirable to amorphicize (e.g., high energy grind) a single calcium phosphate source in order to increase its reactivity or modify its properties in reactions with other calcium phosphate compounds or other agents. Interaction and reaction of the powders also may occur. The amorphicized calcium phosphate powder can be used alone or in combination with conventional calcium phosphates, calcium sources and/or phosphate sources to provide a powder component. The powder component is combined with a hydration medium, such as water, aqueous solution, e.g., saline or phosphate buffer, or serum to form a hardened calcium product.

In one or more embodiments of the invention, two or more powders, at least one of which is a calcium phosphate source, are subjected to the high energy process of the invention. Thus, in one or more embodiments, the powder can include two or more calcium phosphates. In one or more embodiments, the calcium phosphate source is combined with a secondary powder such as a phosphate or a calcium source (or other agent as desired) and subjected to high energy processing to obtain an amorphicized powder. In addition to the effects noted above for a single-component powder, e.g., increased reactivity and reduced crystallinity, high energy grinding of multi-component powders can also promote interaction and reaction between the powders.

The particular manner in which the dry ingredients are combined is not essential to the invention. In one or more embodiments, the calcium phosphate source is amorphicized by high energy milling and the resultant amorphous or nanocrystalline calcium phosphate is combined with conventional dry powders. In one or more embodiments, two or more powder sources are amorphicized, either by high energy milling together or separately. In some embodiments, a calcium phosphate source can be high energy milled and then combined with other dry components by mixing, milling or combining using other conventional processes.

In one or more embodiments, high energy milling is carried out in a container having rotating shafts and/or arms that agitate a grinding media, e.g., milling balls, into a random state of motion. During the milling, the balls are thus projected violently within the container of the mill. The balls also collide with each other within the container. When sufficient mechanical energy is applied to the total charge (balls and powders), a substantial portion of the charge is continuously maintained in a state of relative motion. The grinding media and the particulates are free to move, collide and impinge upon each other, thus generating high shear and powerful impact for efficient grinding. The impact energy developed by these repetitive shocks is sufficient to form nanostructural particles or crystalline domains on the order of about 10 to 100 nanometers. The small particle size of the precursor contributes to a high specific surface area, which contributes to efficient reaction of the powders. For example, the specific surface area of the powder can be between about 50 $m^2/g$ and about 100 $m^2/g$ in the dry powder. By repeating the process, the grinding media breaks down the powder into small particles, and then impinges them on one another to form agglomerates, which can themselves be subject to further impact. Thus, the various particles are evenly mixed and dispersed. Furthermore, the high energy of impact and, optionally, local heating cause both physical and chemical changes in the particles to occur. Due to the small scale of the microstructure and enhanced diffusivity of the species, solid state reactions and/or phase transformations occur during milling or at much lower temperature during subsequent reaction.

Intensive mechanical grinding can be carried out in an attritor, a high energy ball milling machine or any similar piece of equipment. In ball milling, the energy input to the powder charge is provided by the rotation of the mill, cylindrical cell or vial about a horizontal axis. The ball mill can be a planetary milling machine or a horizontal mill. An attritor uses metal arms to stir the powder charge. The intensive mechanical grinding can be carried out in a high-energy ball milling machine like those sold under the trademarks Fritch Pulverisette 4, ASI Uni-Ball Mill II and Zoz Simoloyer®.

The preparation of the nanocrystalline calcium phosphate powder of the invention should not be confused with the conventional steps of milling or grinding to mix a heterogeneous powder or to reduce particle size. Such methods may be carried out in a ball mill, but use much less energy or take steps, e.g. wet grinding, to prevent local heat (energy) generation to accomplish the tasks. There is no change in the atomic structure and/or long range solid state order of the materials in these conventional processes. Furthermore, there is no manipulation of the crystal structure on the nanometer scale, as is observed in the present invention.

The high energy mechanical grinding of the present invention is carried out in such a manner as to reduce the size of the crystallites to a few nanometers. For example, the final crystal size is less than about 100 nm, or less than about 50 nm, or less than about 10 nm. In one or more embodiments, the high energy grinding is carried out at atmospheric pressure under an inert atmosphere for a period of time sufficient to achieve reduction of the crystallite size to the desired value and optionally to cause a chemical and/or structural transformation of the calcium phosphate powder. Chemical transformations include the formation of new chemical entities. Structural transformations include changes on the atomic and lattice level, such as atomic dislocation and lattice defect formation.

In one or more embodiments, amorphization is accomplished using grinding under conditions (grinding time, powder load and grinding medium load, RPM of grinding jar, etc.) that subject the powder to forces sufficient to amorphicize the powder. Grinding conditions can be altered or adjusted so that adequate amorphization takes place in a desired time frame and for a desired powder load. Processing efficiency is affected by grinding time, the amount of powder processed, and ratio of powder to grinding medium (in ball milling processes).

In general, the longer the grinding the time, the greater the extent of amorphization. However, the actual amount of time required is influenced by other factors, such as the type of grinding process used, e.g., ball milling, attrition, grinding, etc., the amount of powder processed and the ratio of powder to grinding medium in ball milling processes. By way of example, 30 grams of a calcium phosphate powder is conventionally processed (SPEX grinding) for 10 minutes without resulting in a solid state fusion of the component powders; however, a smaller sample (e.g., 2 g) that is processed for 20 minutes under similar conditions produces an amorphicized powder according to one or more embodiments of the present invention. By way of further example, a larger powder sample (e.g., 100 g) may require more time (e.g., 96 hours) to achieve the same level of amorphization. In one or more embodiments, grinding is conducted for a period of more than 5 minutes, or more than 10 minutes, or more than 20 minutes, or more than 30 minutes; however, grinding for longer time periods, such as about 1 to 96 hours, or about 1 to 24 hours, is also contemplated.

The greater the ratio of grinding media to powder, the greater the extent of amorphization and/or the shorter the grinding time required for amorphization. In general, low grinding media content (e.g., more than about 50 wt % powder) and short grinding times (e.g., less than 1 hour) do not produce the amorphicized powders according to one or more embodiments of the present invention. The converse is also generally observed, that is, high grinding media content (<50 wt % powder) and longer grinding times (>1 hr) produce amorphicized powders. In one or more embodiments, the grinding media to powder ratio can vary from 10:90 to 90:10 wt/wt. By way of example only, the grinding media to powder ratio can be about 60:40 grinding media: powder.

The powders are ground wet or dry and can be processed under a range of conditions. Dry grinding is employed when the materials are hydroscopic. For wet grinding, water, isopropyl alcohol or other media is used as the liquid medium. The dry grinding process may generate more internal heat than wet grinding due to greater friction in the dry grinding process and cooling may be desired (and is appropriate for wet grinding, as well). In one or more embodiments of the invention, a cooling jacket can be used to control the temperature of milling process. Heat generation also depends on the ratio of milling media to powder. In one or more embodiments, the mill interior (inside wall and arms) is constructed with a ceramic material or a ceramic lining to provide a metal-free grinding process. The grinding media can be any conventional grinding media, for example, ceramic materials such as zirconia or alumina, and for example, having a diameter from about 1 to 20 mm.

The extent of amorphization is monitored by Fourier Transform infrared spectrometry and/or X-ray diffraction spectrometry. Clearly defined peaks in both spectra become broad and poorly defined as crystallinity is reduced as is described in greater detail below. The effectiveness of the grinding process is also evaluated by tap density of the ground powder. Tap density is the density of a powder that is packed into a defined volume. Powders that have been ground to a fine particle size pack more efficiently and have a greater tap density than powders of a greater particle size. The amorphicized powders according to one or more embodiments of the present invention have tap densities of greater than 0.7 g/cm$^3$ (compared to tap densities of less than 0.6 g/cm$^3$ for conventional powders). See, Table 1. The effectiveness of grinding also affects the porosity of a final hardened calcium phosphate cement prepared from a hydrated powder (paste) containing the amorphicized calcium phosphate powder. The amorphicized powders of the present invention pack more efficiently and form less porous calcium phosphate cements than their conventional powder counterparts. A convention calcium phosphate powder prepared from a mixture of amorphous calcium phosphate and dicalcium phosphate dihydrate has a porosity of about 60%. This is compared to a high energy processed powder according to one or more embodiments of the present invention that has a porosity of about 20-30%.

In one or more embodiments of the present invention, the amorphization method according to one or more methods of the present invention provides a single-component, self-setting calcium phosphate cement. A single-component cement, as that term is used herein, means that the calcium phosphate is derived from a single chemical source. A self-setting cement, as that term is used herein, means that the material, when formed as a paste or putty by addition of a hydrating liquid, hardens without addition of heat or other setting agents. Generally in the prior art, self-setting calcium phosphate cements require at least two reactive components, most typically an acid component and a basic component, which react together to promote the hardening process. The amorphization process of the present invention, increases the reactivity of a single calcium phosphate so that it is able to convert and harden without additional calcium, phosphate or calcium phosphate components.

Figure 2B:
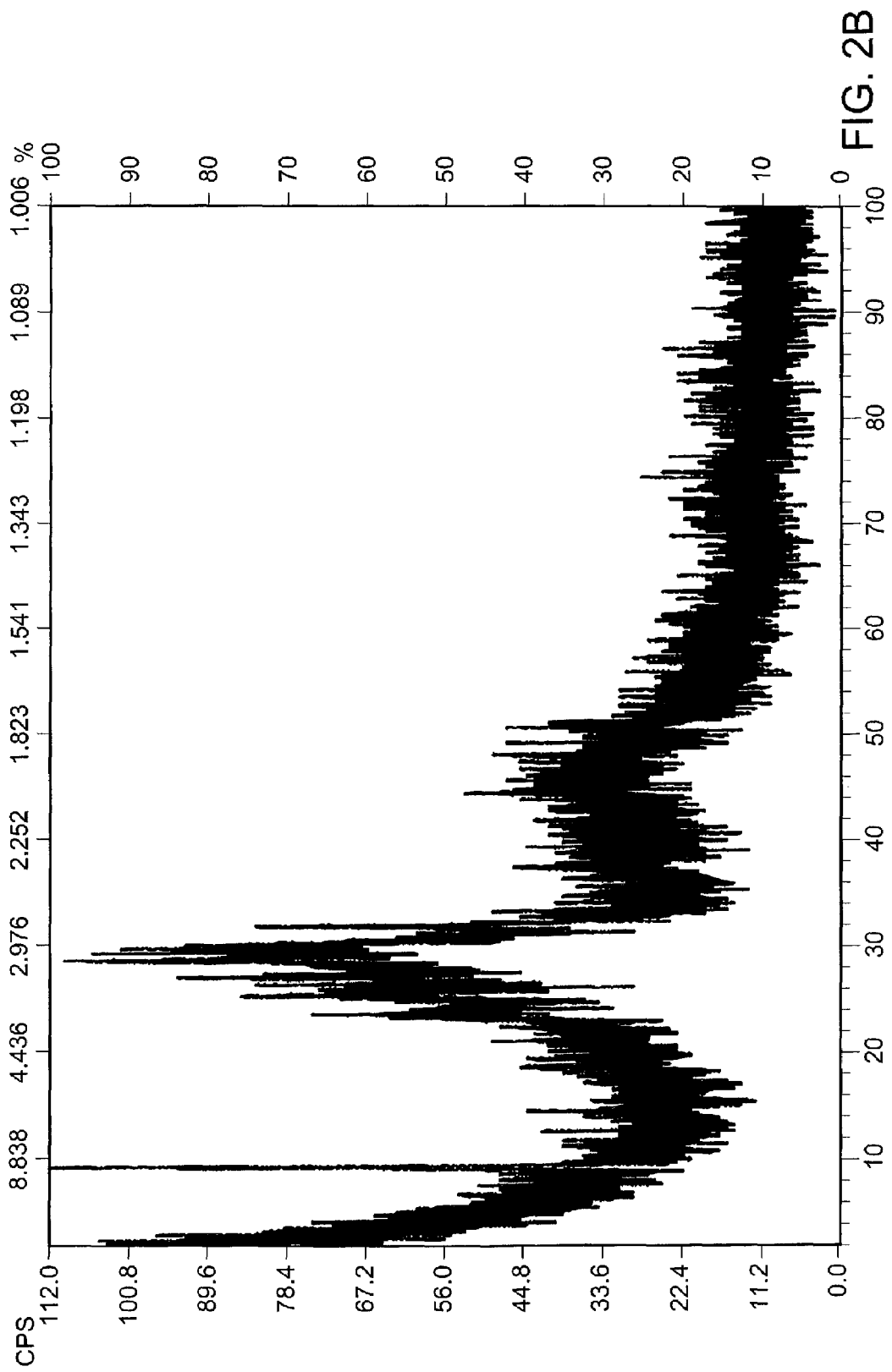

An exemplary single-source self-setting cement includes high energy ball-milled amorphous or nanocyrstalline dicalcium phosphate dihydrate (DCPD) powder. DCPD (128 g), which has been high energy ball milled at 400 RPM for 20 minutes, becomes amorphous as observed by X-ray diffraction (XRD). FIG. 2A is an XRD pattern of an untreated DCPD powder. The pattern exhibits the sharp well-defined peaks that are a signature of a highly crystalline material. FIG. 2B is an XRD pattern of the DCPD powder after high energy milling. Although the sensitivity has been increased 60-fold over that of FIG. 2A, the XRD pattern shows only broad featureless bands barely above background noise—an indication of an amorphous material. A conventional, e.g., crystalline, DCPD paste does not harden or undergo any chemical transformation in the room temperature to body temperature (20-37° C.) range. In contrast, "amorphous DCPD" can be used to form a paste with water that hardens in 30 minutes at body temperature (37° C.) to produce a poorly crystalline apatitic calcium phosphate. A poorly crystalline hydroxyapatite has the chemical composition associated with hydroxyapatitie; however the composition has a very short range of crystalline order (nm). A poorly crystalline hydroxy apatite has a characteristic x-ray diffraction (XRD) pattern that is substantially the same as that of naturally occurring bone. The XRD pattern is characterized by two broad peaks in the 20-35° (2θ) range, with one peak centered at 26° (2θ) and the other centered at 32° (2θ), as is observed in FIG. 2B.

Other amorphous or nanocrystalline calcium phosphates processed according to one or more embodiments of the present invention are expected to demonstrate similar self-setting properties. Suitable calcium phosphates include, but are not limited to, hydroxyapatite, tetracalcium phosphate, octacalcium phosphate and tricalcium phosphates. While not being bound by any particular mode of operation, it is hypothesized that the high energy milling increases the specific surface area of the particles and greatly increases the amount of exposed and reactive surfaces. In one or more embodiments, the local heating may cause reaction of the calcium phosphate resulting in a reactive calcium phosphate mixed phase although this is not an essential feature of the invention. The increased surface reactivity and optional mixed phase composition converts otherwise unreactive components into reactive species and permit conversion into a hardened product proceeds at room to body temperature (20-37° C.). The nature of the product calcium phosphate will depend, in part, on the Ca:P atomic ratio of the starting amorphicized powder. For example, compositions having a Ca:P ratio approximating hydroxyapatite of a calcium deficient apatite, e.g., Ca:P atomic 1.40-1.70, tend to form a poorly crystalline hydroxyapatite. The end produce can be hydroxyapatite, poorly crystalline hydroxyapatite, or other forms of calcium phosphate, such as tetracalcium phosphate, tricalcium phosphate, octacalcium phosphate and the like.

In one or more embodiments of the present invention, the amorphicized calcium phosphate powder is combined with one or more other solid components, e.g., calcium phosphates, Ca sources and/or phosphate sources, to form a self-setting calcium phosphate cement.

In one or more embodiments, two or more solids, including at least one calcium phosphate, are combined and amorphicized to obtain a low crystallinity calcium phosphate powder useful as a self-setting calcium phosphate cement. Suitable calcium phosphates include, but are not limited to, one or more of amorphous calcium phosphates, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate and tricalcium phosphates. Suitable calcium sources include but are not limited to calcium carbonate, calcium hydroxide, and calcium oxide. The powders are combined in a ratio of 1:100 to 100:1, or about 1:10 to 10:1 or about 1:5 to 5:1 or about 1:1 to obtain a starting powder of the desired composition.

In one or more embodiments, a carbonated, poorly crystalline hydroxyapatite is obtained using the methods and materials according to one or more embodiments of the present invention. Carbonated, poorly crystalline hydroxyapatite is a desirable product because it closely mimics the composition of natural bone (which has a carbonate component). A calcium phosphate such as dicalcium phosphate dihydrate (Ca:P of 1.0) and calcium carbonate are combined in a proportion to provide a Ca:P atomic ratio of about 1.4-1.7, or about 1.4-1.6. For example, a powder containing 70 wt % dicalcium phosphate dihydrate and 30 wt % $CaCO_3$ gives a final Ca:P of about 1.67. The combined powders are high energy ground to form an amorphicized powder that incorporates the carbonate into the calcium phosphate powder. The amorphicized powder is used to prepare a self-setting cement that hardens and is converted into a carbonated, poorly crystalline hydroxyapatite. See Example 2.

In at least some embodiments, at least one of the materials in the precursor is an amorphous calcium phosphate. Amorphous calcium phosphate is formed by rapid precipitation from a solution containing calcium and phosphate ion sources, which produces very small calcium phosphate nuclei having many defects. Amorphous calcium phosphate initially is formed as a gel-like solid, which can be collected and dried to provide a fine, homogeneous powder. Amorphous calcium phosphate includes solids of varying composition, has a broad, diffuse X-ray diffraction pattern, lacks long-range structure, and is homogeneous when measured on an Angstrom scale.

Amorphous calcium phosphate has a Ca/P ratio in the range of about 1.1 to about 1.9. In some embodiments, the Ca/P ratio is between about 1.35 and about 1.65. In particular embodiments, the Ca/P ratio is between about 1.50 and about 1.58. In some embodiments, the Ca/P ratio is less than about 1.50. In particular embodiments, the Ca/P ratio is between about 1.35 and about 1.49. Preparation and characterization of amorphous calcium phosphates is described in detail in U.S. Pat. No. 6,214,368, which is incorporated herein by reference. One method of preparing amorphous calcium phosphate is set forth in Example 3 below.

In at least some embodiments, an amorphous calcium phosphate is combined with at least one other calcium phosphate in the calcium phosphate powder. While amorphous calcium phosphate does not require high energy milling in order to reduce crystallinity, milling with a second calcium phosphate improves reactivity and hardening properties of the resultant powder. Appropriate second calcium phosphates for use in the calcium phosphate precursor of the invention include acidic, basic, and neutral calcium phosphates having the correct stoichiometry for reaction to obtain apatitic calcium phosphate. Suitable second calcium phosphates include, but are not limited to, one or more of amorphous calcium phosphates, hydroxyapatite, carbonated apatite (calcium-deficient hydroxyapatite), monocalcium phosphate, calcium metaphosphate, heptacalcium phosphate, dicalcium-phosphate dihydrate, tetracalcium phosphate, octacalcium phosphate, calcium pyrophosphate and tricalcium phosphates.

In at least some embodiments, the first calcium phosphate of a two-component calcium phosphate powder is neutral, e.g., having a pH between about 6.5 and about 7.5, and the second calcium phosphate is acidic, e.g., having a pH less than about 6.5. Exemplary acidic calcium phosphates include dicalcium phosphate dihydrate, calcium metaphosphate, heptacalcium phosphate, monocalcium phosphate and octacalcium phosphate. Exemplary neutral calcium phosphates include amorphous calcium phosphate.

In still other embodiments of the present invention, the amorphicized calcium phosphate powder may contain other ingredients, which can be added before or after high energy milling. For example, a calcium phosphate powder may be combined with a calcium source or a phosphate source to provide a powder having a desired overall calcium to phosphate atomic ratio (Ca:P). The Ca:P atomic ratio may be that of a desired product calcium phosphate, such as for example, a calcium-deficient hydroxyapatite. Calcium-deficient hydroxyapatite can have a Ca:P atomic ratio of about 1.4-1.75, and can have a Ca:P ratio of about 1.5-1.6. By way of example, amorphicized DCPD (Ca:P=1.0) is combined with a calcium source such as $CaCO_3$ to raise the calcium content of the powder and have the carbonate group in the structure.

The amorphicized calcium phosphate powder of the invention is used in the preparation of self-setting calcium phosphate cements. A hydrating medium is added to the powder component to form a putty or paste. Suitable hydrating media include aqueous solutions, including water, saline, serum and physiologically acceptable buffers, e.g., phosphate buffers and the like. A hydrating medium is used in an amount suitable to provide a paste of the desired consistency, and typically in used in a 5:1 to 1:5 powder:hydrating medium weight ratio. In one or more embodiments, the paste includes 2:1 to 1:2 powder:hydrating medium, or about 1:1 powder:hydrating medium.

It has been discovered that the use of amorphicized calcium phosphate powder in a self-setting calcium phosphate cement provides a hardened calcium phosphate of low crystallinity and high compressive strength. Low crystallinity is desirable for improving bioresorbability of the calcium phosphate. The compressive strength improves the mechanical integrity of the hardened product. Compressive strength of various hardened calcium phosphate products is listed in Table 1, below. Examples T20 and AB1-AB4 represent calcium phosphate products prepared using the amorphicized calcium phosphate powders of the invention. These hardened products had a measured compressive strength of greater than 20 MPa and as high as about 50 MPa, and in particular 30-50 MPa. High compressive strength is desired in an implant material in many weight bearing applications. The higher compressive strength of the calcium phosphate material permits addition of supplemental materials without unacceptable loss of mechanical properties. The hardened calcium phosphate products may have porosities in the range of about 20-30%.

The nanocrystalline calcium phosphate phase in its initial paste form typically maintains a pH of about 6-8 and is therefore compatible with a wide range of additives without deleterious effect. A supplementary material is selected based upon its compatibility with calcium phosphate and its ability to impart properties (biological, chemical or mechanical) to the composite, which are desirable for a particular therapeutic purpose. For example, the supplementary material or additives may be selected to improve tensile strength and hardness, increase fracture toughness, alter elasticity, provide imaging capability, and/or alter flow properties and setting times of the bone substitute material. The supplementary materials are desirably biocompatible, that is, there is no detrimental reaction induced by the material when introduced into the host.

The supplementary material may be added to the amorphicized calcium phosphate in varying amounts and in a variety of physical forms; it may added to the dry powder or the hydrated paste form; it may be added before or after high energy ball milling, dependent upon the anticipated therapeutic use. The supplementary material may be in the form of sponges (porous structure), meshes, films, fibers, gels, filaments or particles, including micro- and nanoparticles. The supplementary material itself may be a composite. The supplementary material may be used as a particulate or liquid additive or doping agent that is mixed intimately with the amorphicized calcium phosphate powder or hydrated paste thereof. The supplementary material is added at a volume fraction of 0.1-50 vol %, or about 1-20 vol % in solid and/or solution form.

In one or more embodiments of the present invention, the supplementary material is bioresorbable. In one or more embodiments of the present invention, the supplementary material has an affinity for calcium, phosphate or calcium phosphates that will enhance the strength of the calcium phosphate/supplementary material interface. The affinity may be specific or mediated through non-specific ionic interactions. Suitable bioerodible polymers for use as a matrix in the composite include, but are not limited to, collagen, glycogen, chitin, celluloses, starch, keratins, silk, nucleic acids, demineralized bone matrix, derivativized hyaluronic acid, polyanhydrides, polyorthoesters, polyglycolic acid, polylactic acid, and copolymers thereof.

In one or more embodiments, polyesters of alpha-hydroxycarboxylic acids, such as poly(L-lactide) (PLLA), poly (D,L-lactide) (PDLLA), polyglycolide (PGA), poly(lactide-co-glycolide) (PLGA), poly(D,L-lactide-co-trimethylene carbonate), and polyhydroxybutyrate (PHB), and polyanhydrides, such as poly(anhydride-co-imide) and co-polymers thereof are suitable for use in the present invention. In addition, bioactive glass compositions, such as compositions including $SiO_2$, $Na_2O$, $CaO$, $P_2O_5$, $Al_2O_3$ and/or $CaF_2$, may be used in combination with the low crystallinity calcium phosphate of the present invention. Other useful bioerodible polymers may include polysaccharides, peptides and fatty acids. Bioerodible polymers are advantageously used in the preparation of resorbable hardware, such as pins, screws, plates and anchors for implantation at a bone site. In preferred resorbable hardware embodiments, the supplementary material itself is resorbable and is added to the low crystallinity calcium phosphate in particulate or fiber form at volume fractions of 1-50% and preferably, 1-20 wt %. In one or more embodiments, the resorbable fiber is in the form of whiskers, which interact with calcium phosphates according to the principles of composite design and fabrication known in the art. Such hardware may be formed by pressing a powder particulate mixture of low crystallinity calcium phosphate and polymer.

The resorbable nature of the self-setting calcium phosphate cement of the present invention and its ability to benignly interact with and adsorb proteins, nucleic acids, and other substances make it an ideal substance for use as an implantable depot for use in the delivery of therapeutic substances to the body. In general, the main requirement is that the agent to be delivered remains active in the presence of the vehicle during fabrication and/or loading, or be capable of subsequently being activated or reactivated. The stability and/or compatibility of a particular agent with the inventive material, as well as fabrication strategies, may be tested empirically in vitro. Some representative classes of useful biological agents include organic molecules, proteins, peptides, nucleic acids, nucleoproteins polysaccharides, glycoproteins, lipoproteins, and synthetic and biologically engineered analogs thereof.

In one aspect of the invention, bone regenerative proteins (BRP) are incorporated into the calcium phosphate. BRPs have been demonstrated to increase the rate of bone growth and accelerate bone healing. A bone graft including the calcium phosphate and BRP is expected to promote bone healing even more rapidly than a bone graft using the calcium phosphate of the present invention alone. The efficacy of BRP is further enhanced by controlling calcium phosphate resorption such that it dissolves at a rate that delivers BRP, calcium, and phosphorus at the optimum dosage for bone growth.

Such a method of incorporating BRP would include, but not limited to, mixing a buffer solution containing BRP at the optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenctic Proteins. Such BRPs are currently being developed by Genetics Institute, Cambridge, Mass.; Genentech, Palo Alto, Calif.; and Creative Biomolecules, Hopkinton, Mass.

In another embodiment of the invention, it is contemplated to incorporate antibiotics or agents into the amorphicized calcium phosphate powder. From a clinical sense, one of the major implications arising from a bone-graft surgery is a need to control the post-operative inflammation or infection. A bone graft including the calcium phosphate and antibiotic(s) is expected to reduce the chances of local infection at the surgery site, contributing to infection-free, thus faster bone healing process. Exemplary antibiotics include, but are in no way limited to, Penicillin, Chlortetracycline hydrochloride (Aureomycine), Chloramphenicol and Oxytetracycline (Terramycine). Both antibiotics, most polypeptides, and bone regenerating proteins may be intermixed with the calcium phosphate material of the present invention, to locally deliver all or most of the necessary components in facilitating optimum condition for bone tissue repair.

The invention is illustrated by the following examples, which are not intended to be limiting of the invention.

EXAMPLE 1

Preparation of a Self-Setting Dicalcium Phosphate Dihydrate Cement

The example describes the amorphization of dicalcium phosphate dihydrate according to one or more embodiments of the present invention.

Crystalline dicalcium phosphate dihydrate (DCPD), which is used in the preparation of the nanocrystalline calcium phosphate powders of the present invention, was prepared as follows.

DCPD was prepared at room temperature by the rapid addition of a solution of calcium nitrite tetrahydrate (17.1 g in 250 mL distilled water) into a solution of diammonium hydrogen phosphate (10 g in 500 mL distilled water at a pH of 4.6-4.8) with constant stirring. Immediately thereafter, the sample was filtered using filter paper (0.05 sq. ft) with medium filter speed and a vacuum pressure of about $10^{-2}$ torr. The material formed a thin cake, which was washed with about 2 liters of distilled water and then dried at room temperature for 24-72 hours. A highly crystalline DCPD was obtained.

DCPD was amorphicized by high energy ball milling in a Attritor Model 01HD (Union Process) ball mill. In a 1400 mL stainless steel tank having a 2 cm thick alumina lining was added 750 mL of grinding media (5 mm diameter high purity yttria-stabilized zirconium oxide) and 300 mL (about 128 g or 40 vol %) DCPD. The powder was milled at 400 RPM for 5 minutes, after which 5 mL of isopropyl alcohol was added. Grinding was resumed for a total grinding time of 20 minutes. The ground material was discharged and separated from the grinding media by sieving through a 5 mm diameter sieve. Some caking of the powder on the ceramic mill walls was observed.

Figure 3A:
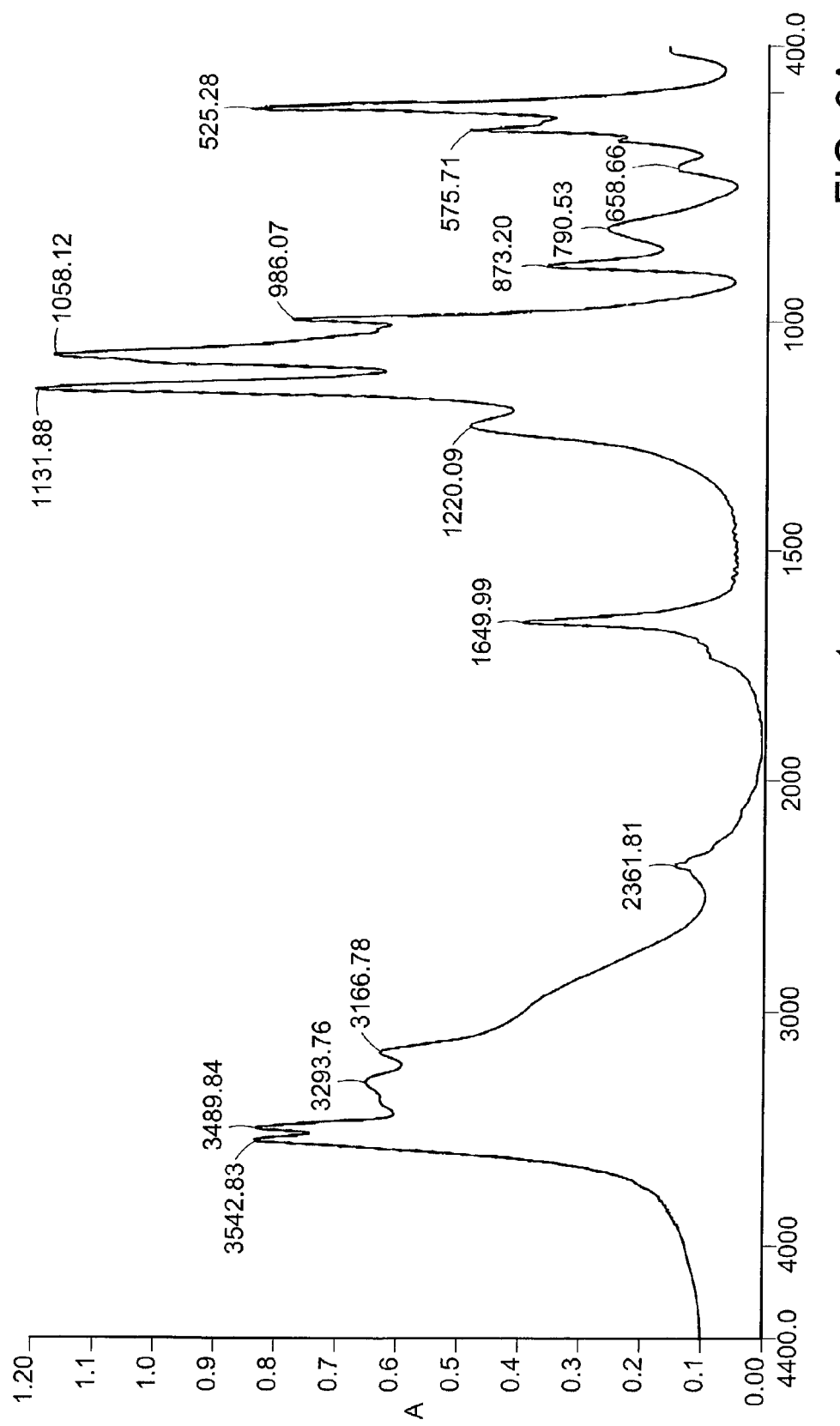
FIGS. 3A-3C show the Fourier Transform infrared (FTIR) spectrum of dicalcium phosphate dihydrate (DCPD) (3A) before grinding, (3B) as a nanocrystalline powder after grinding, and (3C) after adding the hydration media in the carbonate buffer, hardening as a cement and transforming into poorly crystalline apatitic calcium phosphate according to one or more embodiments of the present invention.
Figure 3B:
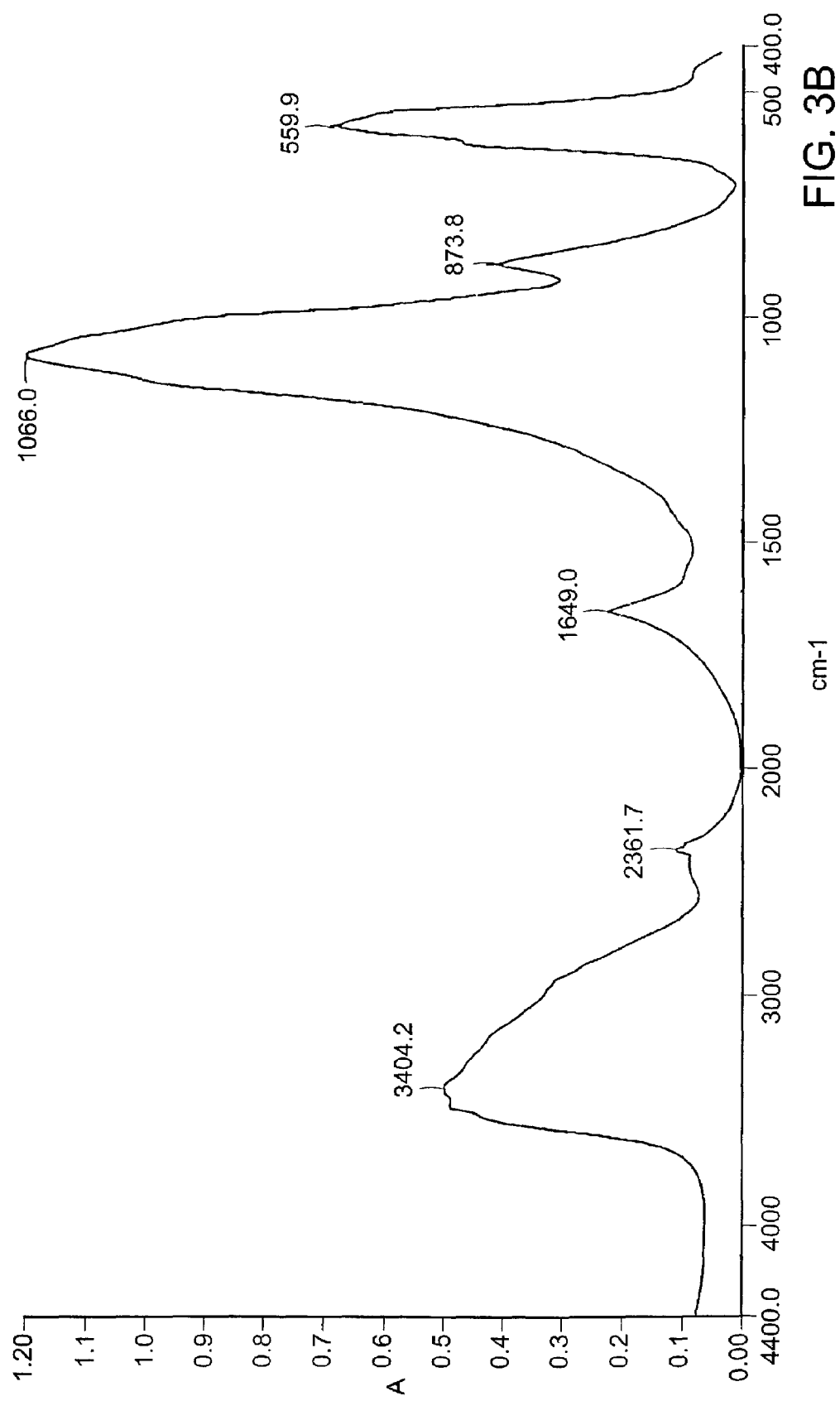

The resultant powder was characterized in the following ways. The Coulter particle size of the sample was measured before and after grinding, showing a reduction in particle size from 25 µm to 7 µm. The extent of amorphization (reduction in crystallinity) was monitored by XRD (see, FIGS. 2A-2B) and FTIR (FIGS. 3A-3B), which established that the high energy ground powder had crystalline domains of less than 100 nm. FIG. 3 shows the FTIR spectrum of DCPD before grinding (3A) and after grinding (3B). FIG. 3A shows clearly defined bands particularly in the 3000-4000 $cm^{-1}$, 1000-1200 $cm^{-1}$ and 500-650 $cm^{-1}$ regions and total disappearance of the peak at 790.5 $cm^{-1}$. After high energy grinding, the bands are broad and poorly defined. See, FIG. 3B. This most likely indicates formation of new species whose bands overlap those of DCPD and/or the increasing amorphicity of DCPD, which results in broadening of the bands.

Figure 3C:
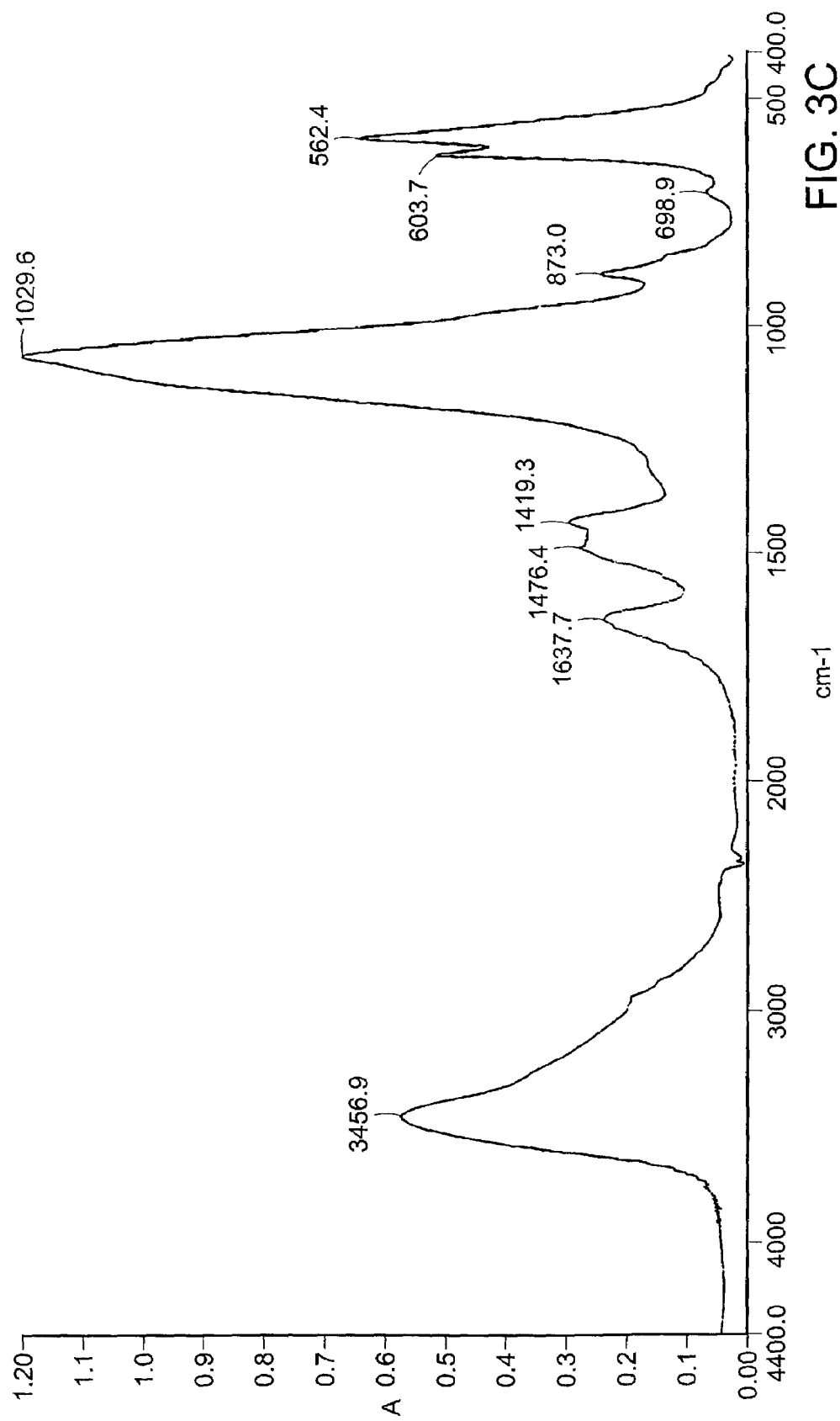

An amorphicized DCPD paste was formed with saline solution (1 g solid in 0.55 mL saline) and the paste was incubated at 37° C. in a moist environment for 30 minutes. A hardened calcium phosphate was obtained. FIG. 3C shows the FTIR spectrum of the DCPD self-setting cement after conversion in a carbonate buffer. Note that some peaks have shifted (e.g., 1649.0 $cm^{-1}$ to 1637.7 $cm^{-1}$) and new peaks have appeared at 603.7 $cm^{-1}$, which is characteristic of a poorly crystalline apatitic calcium phosphate. This indicates that the DCPD self-setting cement has undergone chemical transformation to form a calcium deficient apatitic calcium phosphate.

EXAMPLE 2

Preparation of Carbonated Apatitic Cement

This example describes the preparation and reaction of an amorphicized calcium phosphate powder prepared from DCPD and $CaCO_3$ according one or more embodiments of the present invention.

Crystalline DCPD, prepared as described above in Example 1, and commercial calcium carbonate ($CaCO_3$) were combined in a 90:10 DCPD:$CaCO_3$ (wt/wt) ratio to provide a calcium to phosphate ratio of 1.5-1.6.

Figure 4A:
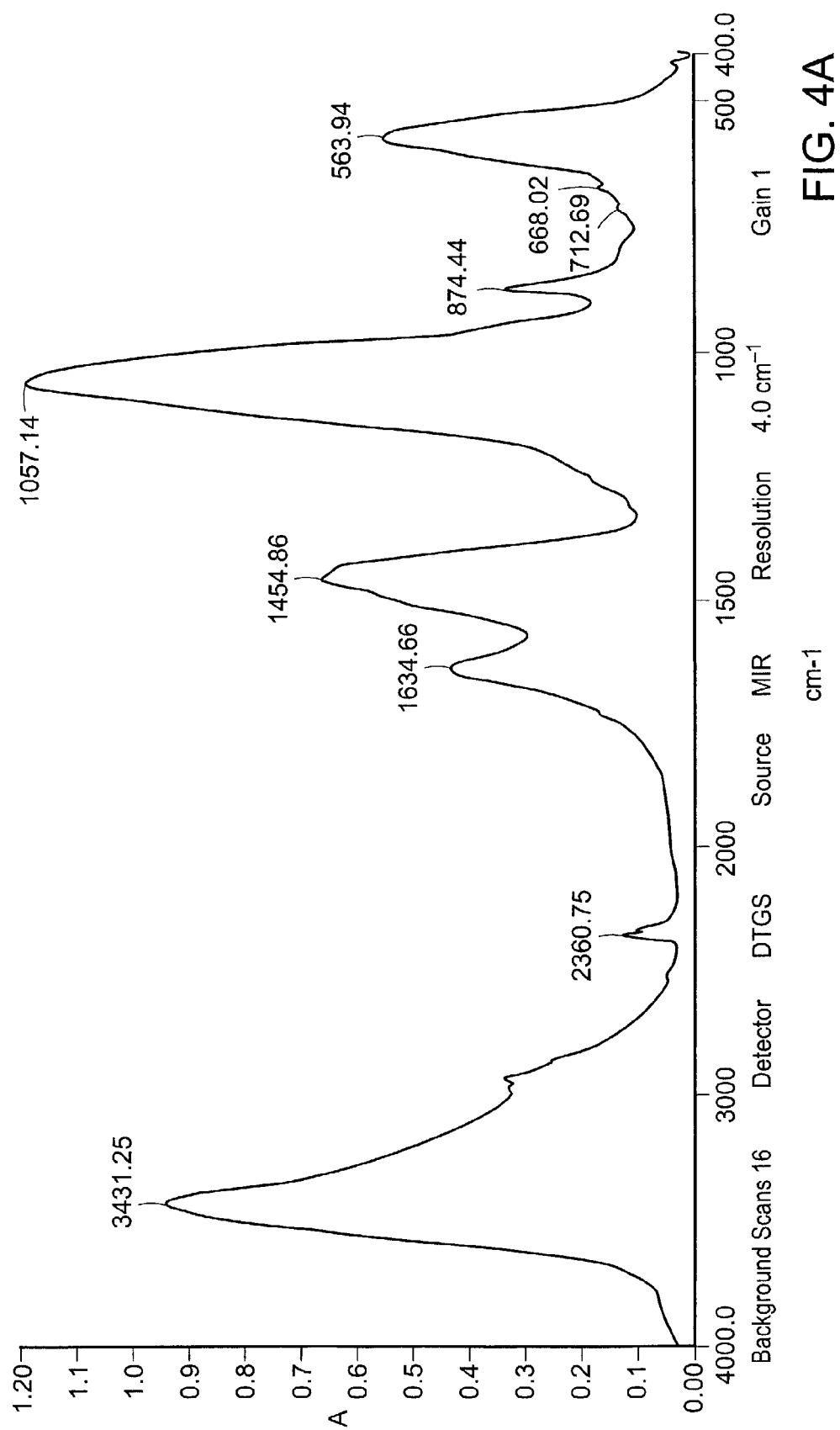
FIGS. 4A and 4B show the Fourier Transform infrared (FTIR) spectrum (4A) of a nanocrystalline powder prepared from dicalcium phosphate dihydrate and calcium carbonate and (4B) of the powder after its conversion to a poorly crystalline hydroxy apatite after hydration and incubation at body temperature according to one or more embodiments of the present invention.

About 100 g of the above powder was charged into a high energy ball mill and was dry ground for 62 hours to obtain a homogeneous powder having a Ca:P ratio of 1.5-1.6. The resultant powder was characterized in the following ways. The extent of amorphization (reduction in crystallinity) was monitored by Fourier Transform intrared spectroscopy (FTIR) and X-ray diffraction (XRD). The FTIR of the resultant powder is shown in FIG. 4A. Note that the bands have the same broad features as the nanocrystalline DCPD powder of FIG. 3B; additional bands are attributed to $CO_3$ at 1454.9 $cm^{-1}$.

Figure 4B:
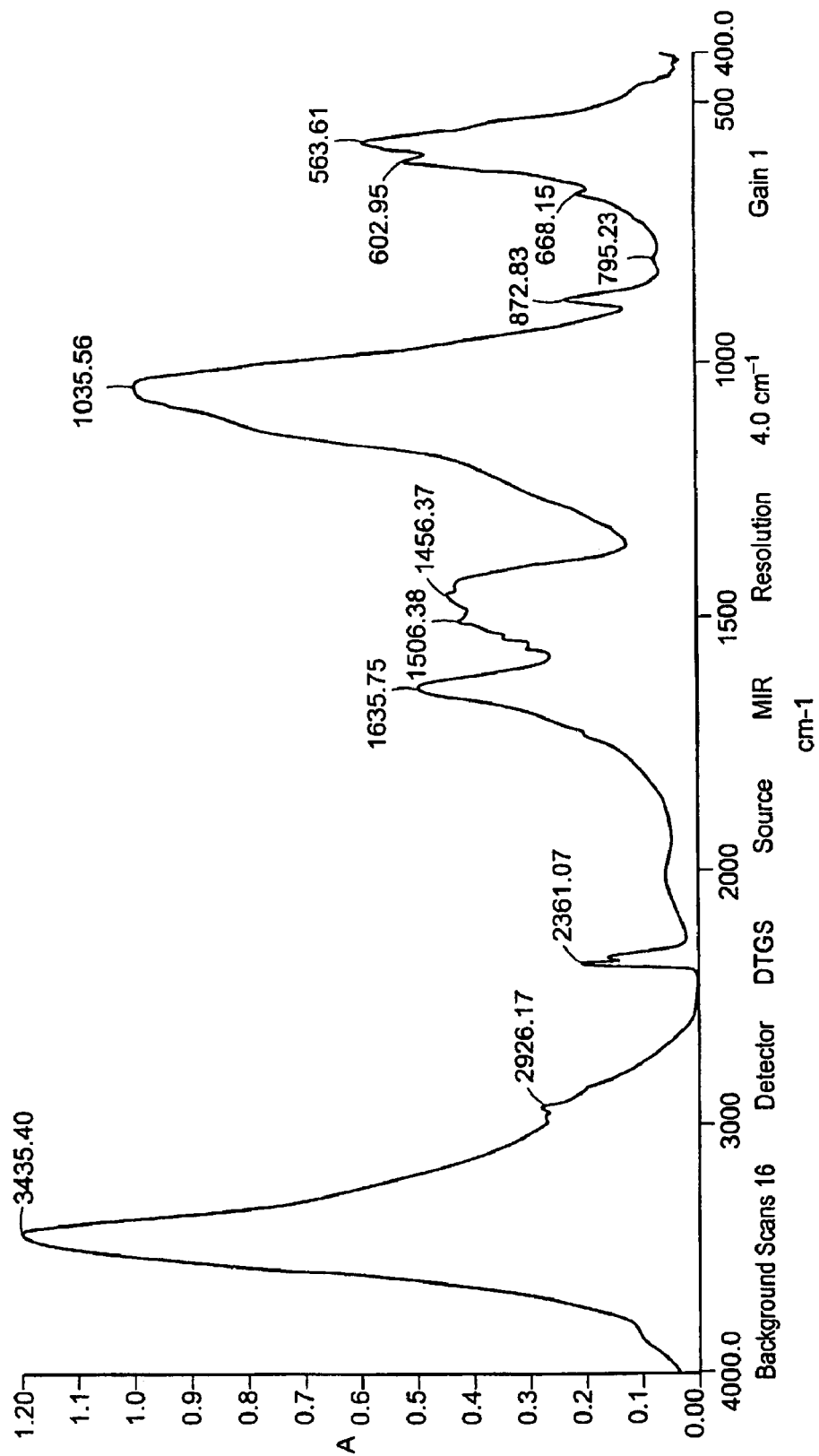
Figure 5:
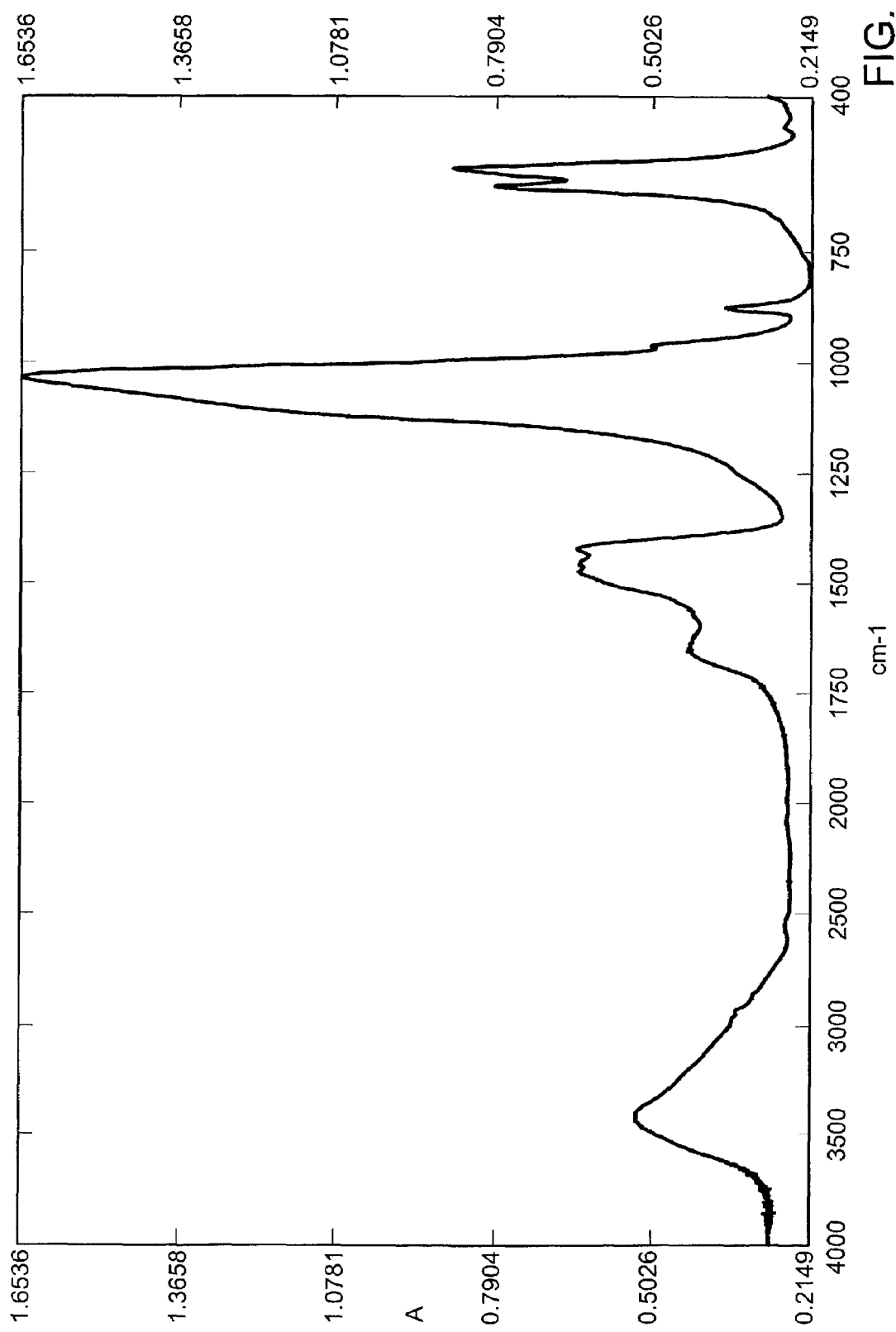
FIG. 5 is a Fourier Transform infrared (FTIR) spectrum of natural bone.

A paste was formed using amorphicized DCPD/$CaCO_3$ in saline solution (1 g solid in 0.38 mL saline) and the paste was incubated at 37° C. in a moist environment. The paste hardened after 30 minutes and was converted into a carbonated apatite (FIG. 4B) after 24 hours having a calcium phosphate composition very close to the natural bone (FIG. 5). The compressive strength of hardened carbonated apatite was monitored over time. The article achieved full compressive strength of over 20 MPa after 8 h incubation.

EXAMPLE 3

Preparation of High Strength Calcium Phosphate Cement

This example describes the formation of a nanocrystalline powder prepared using two calcium phosphate powders.

A two component calcium phosphate powder was prepared from amorphous calcium phosphate (ACP) and crystalline DCPD. Crystalline DCPD as described in Example 1 was used.

Amorphous calcium phosphate was prepared as follows. A solution of 150 g disodium hydrogen phosphate heptahydrate ($Na_2HPO_4 \cdot 7H_2O$) in 2167 mL distilled water was prepared and stirred. 83.3 g NaOH, 50 g $NaHCO_3$, and 3.3 g sodium pyrophosphate decahydrate ($Na_4P_2O_7 \cdot 10H_2O$) were added sequentially to the solution to form solution 1.

A solution of 31.2 g calcium nitrate tetrahydrate ($Ca(NO_3)_2 \cdot 4H_2O$) in 833 mL distilled water was prepared and stirred. 1.7 g magnesium chloride hexahydrate ($MgCl_2 \cdot 6H_2O$) was added to the solution to form solution 2.

Solution 2 was poured quickly into solution 1 at room temperature and stirred for 1 minute. Precipitation was immediate and substantially complete. The pH of the suspension was 13±0.5, which was maintained to avoid conversion of the precipitate to an apatite or other more crystalline calcium phosphate. The precipitate was promptly separated from its mother solution using a basket centrifugal filtration and washed with about 15 L distilled water. Completion of washing was confirmed by the last wash ionic conductivity <300 µs. A gel cake of about 500 g amorphous calcium phosphate was obtained. The wet cake was immediately lyophilized to preserve the amorphous structure during drying, which removed about 80% of the water. About 100 g of the lyophilized powder was calcinated at 450° C. for 1 hour. The Ca/P ratio of the product was less than 1.5, and typically 1.35-1.49.

Figure 6A:
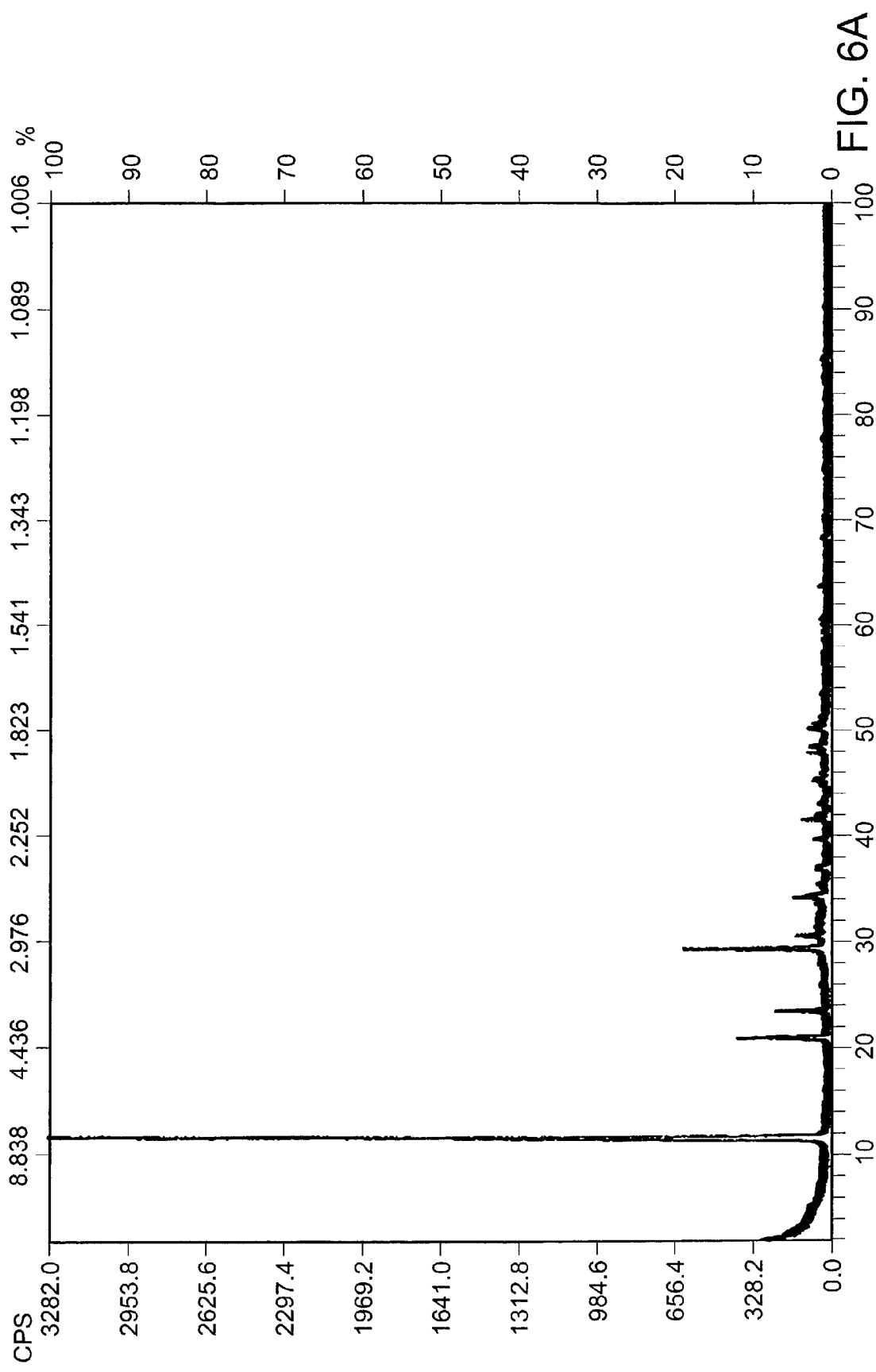
FIGS. 6A and 6B illustrate the X-ray diffraction (XRD) pattern of a two-component powder including dicalcium phosphate dihydrate (DCPD) and amorphous calcium phosphate (6A) before and (6B) after high energy milling at 400 RPM for 10 minutes in a high energy ball mill.
Figure 6B:
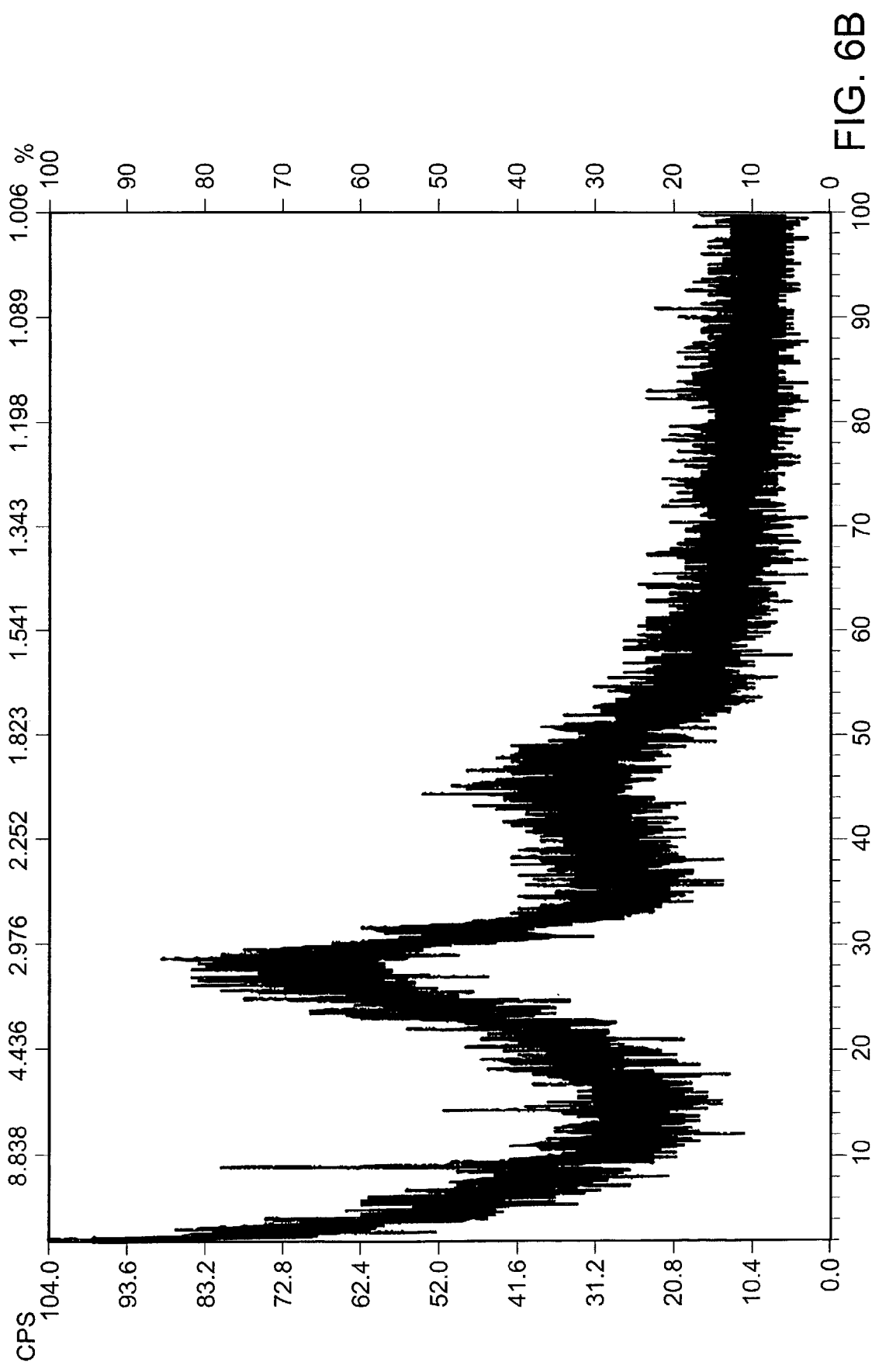

100 g of crystalline DCPD and amorphous calcium phosphate (1:1 by weight) were combined and the mixed powder was high energy milled in a Attritor Model 01HD under the following conditions: (1) Sample T20; 850 RPM conventional ball mill (SPEX) for 20 minutes; (2) Sample AB1; 350 RPM for 5 minutes, (3) Sample AB2; 350 RPM for 10 minutes, and (4) Sample AB3; 400 RPM for 10 minutes. FIGS. 6A-6B demonstrate the amorphization process on the two-component powder AB3. FIG. 6A is an XRD pattern of an untreated AB3 powder. FIG. 6B is an XRD pattern of the AB3 powder after high energy milling. The pattern shows only broad featureless peaks barely above background noise—an indication of crystallite domains on the nanometer scale. FIG. 7A is an FTIR spectrum of a conventionally processed amorphous calcium phosphate/DCPD powder such as T10 in Table 1. In FIGS. 7B-7D, the amorphization rate (crystallization index) for the high energy grinding of the same sample after 3, 5 and 24 hours is observed.

EXAMPLE 4

This example investigates the setting and mechanical properties of calcium phosphate cements.

The setting and mechanical properties of the high energy milled powders (ACP:DCPD) of Example 3 (T20, AB 1, AB2, AB3), the amorphicized DCPD:CaCO$_3$ powder of Example 2 (AB4) and were compared to those of conventionally processed powders T10. Conventional powders include the two-component powder of ACP and crystalline DCPD that were mixed in a conventional mill (SPEX 8520 Shatterbox) for 10 minutes (T10) at 850 RPM. Under these conditions, the powders are mixed and some diminution in particle size was observed, but there was no significant reduction in crystallinity or mechanical alloying of the powder.

The powders were combined with water to form a paste, and the paste was held in a moist environment (by wrapping in a moist tissue) for 30 minutes at 37° C. Setting times, hardness of the set paste and its conversion to a poorly crystalline or calcium deficient hydroxyapatite were evaluated. The injectability and viscosity of the paste were also noted. The results of these characterizations are presented in Table 1.

phosphate, dicalcium phosphate dihydrate, tetracalcium phosphate, octacalcium phosphate, calcium pyrophosphate and tricalcium phosphate, wherein said calcium phosphate is the only source of calcium and phosphate ions in said paste and said powder has an average crystalline domain size of less than about 100 nm and a tap density of greater than 0.7 g/cm$^3$; and a carrier fluid in an amount sufficient to form said paste, wherein said paste is capable of hardening at body temperature in less than 30 minutes.

2. The paste of claim 1, wherein the hardened paste has a compressive strength of greater than 20 MPa after curing at 37° C. for 4 hours.

3. The paste of claim 1, wherein the calcium phosphate is dicalcium phosphate dihydrate.

4. The paste of claim 1, wherein the carrier fluid is a physiologically acceptable aqueous solution.

5. The paste of claim 1, wherein the carrier fluid comprises 20 wt % to 80 wt % of the paste.

6. The paste of claim 1, wherein the crystalline domain size is less than 50 nm.

7. The paste of claim 6, wherein the crystalline domain size is 10 nm.

8. The paste of claim 1, wherein the hardened paste has a compressive strength of greater than 20 MPa after curing at 37° C. for 4 hours.

TABLE 1

| Sample | Grinding (type;[1] time; speed) | Liquid[2] | Hardness[3] | Measured hardness (Kgf) | Injectability[4] (%) | Viscosity[5] (poise) | Paste hardness at 5 min. (Kgf) | Compress strength (MPa) d | Mean | S.D. | Tap density (g/cm$^3$) | FTIR-fully converted |
|---|---|---|---|---|---|---|---|---|---|---|---|---|
| T10 | C; 10; 850 | 0.68 | Hard | 18 | 100 | 7-200 × 10$^5$ | 0.6 | | 8-20 | | 0.56 | PCHA[6] |
| T20 | HE; 20; 850 | 0.42 | Very hard | 70.2 | 0 (100% at 0.5 mL) | 1.1 × 10$^7$ | 10 | 8 | 36.0 | 3.0 | ND | PCHA |
| AB1 | HE; 5; 350 | 0.44 | Very hard | 87.8 | 50 (100% at 0.48 mL) | 6.4 × 10$^6$ | 8.6 | 8 | 37.6 | 5.5 | 0.71 | PCHA |
| AB2 | HE; 10; 350 | 0.44 | Very hard | 74.2 | 50 (100% at 0.48 mL) | 7.6 × 10$^6$ | 10 | 7 | 40.6 | 7.2 | 0.79 | PCHA |
| AB3 | HE; 10; 400 | 0.44 | Very hard | 43.7 | 50 (100% at 0.48 mL) | 5.7 × 10$^6$ | 10 | 14 | 34.2 | 10 | 0.84 | PCHA |
| AB4 | DCPD:CaCO$_3$ 62:400 | 0.38 | Very hard | ND | 100% at 0.45 mL | ND | ND | | 23 (8 h) | | ND | PCHA |

[1]C = conventional ball mill; HE = high energy ball mill; time in minutes; and speed in RPM.
[2]Water by weight added to 1 g of powder sample.
[3]Qualitative determination of hardness after 30 minutes at 37° C. in moist environment.
[4]Quantitative determination of injectability using Texture Analysis
[5]Viscosity of the paste is measured by viscosimeter
[6]PCHA = poorly crystalline hydroxyapatite As will be apparent to one of skill in the art from a reading of this disclosure, the present invention can be embodied in forms other than those specifically disclosed above without departing from the spirit or essential characteristics of the invention. The particular embodiments of the invention described above are, therefore, to be considered as illustrative and not restrictive. The scope of the invention is as set forth in the appended claims, rather than being limited to the examples contained in the foregoing description.

What is claimed is:

1. A calcium phosphate self-setting paste, comprising:
   a powder consisting of a single calcium phosphate selected from the group consisting of monocalcium phosphate, calcium metaphosphate, heptacalcium 9. The paste of claim 8, wherein the hardened paste has a compressive strength of 30 to 50 MPa after curing at 37° C. for 4 hours.

10. The paste of claim 1, wherein the paste is fully converted to poorly crystalline hydroxyapatite or calcium deficient hydroxyapatite in a moist environment at body temperature (37° C.).

11. The paste of claim 1, wherein the calcium phosphate is mechanically alloyed.

12. The paste of claim 1, wherein the hardened paste has a porosity in the range of 20 to 30%.

13. The paste of claim 1, wherein the paste is fully converted to poorly crystalline hydroxyapatite or calcium deficient hydroxyapatite in a moist environment at body temperature (37° C.).

14. The paste of claim 1 further comprising a supplementary material.

15. The paste of claim 14, wherein said supplementary material is selected from a bioerodible polymer, a polyester, a bone regenerative protein, or an antibiotic.

16. The paste of claim 15, wherein said bioerodible polymer is selected from collagen, glycogen, chitin, a cellulose, starch, a keratin, silk, a nucleic acid, demineralized bone matrix, hyaluronic acid, a polysaccharide, a peptide, and a fatty acid.

17. The paste of claim 15, wherein said polyester is selected from an alpha-hydroxycarboxylic acid, a polyhydroxybutyrate, a polyanhydride, and a polyorthoester.

18. The paste of claim 17, wherein said alpha-hydroxycarboxylic acid is selected from polyglycolic acid and polylactic acid.

19. The paste of claim 17, wherein said aipha-hydroxycarboxylic acid is selected from poly(L-lactide), poly(D,L-lactide), polyglycolide and polylactide-coglycolide, and poly(D,L-lactide-co-trimethylene carbonate).

20. The paste of claim 17, wherein said polyanhydride is poly(anhydride-co-imide).

* * * * *